(12) United States Patent
Moein

(10) Patent No.: US 6,547,767 B1
(45) Date of Patent: Apr. 15, 2003

(54) SYRINGE ASSEMBLY FOR A CATHETER

(75) Inventor: Mohammed E. Moein, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 81 days.

(21) Appl. No.: 09/712,350

(22) Filed: Nov. 14, 2000

(51) Int. Cl.$^7$ ............................ A61M 5/00; A61M 25/00
(52) U.S. Cl. ........................................ 604/264; 606/145
(58) Field of Search ........................... 604/19, 96.01, 604/188, 164.01, 915, 103.01, 528, 164.11, 263, 177, 101.03; 606/145, 146

(56) References Cited

U.S. PATENT DOCUMENTS

| 4,161,177 A | * | 7/1979 | Fuchs ........................ 604/177 |
| 5,248,301 A | * | 9/1993 | Koenig et al. ........... 604/164.01 |
| 5,354,279 A | | 10/1994 | Höfling ...................... 604/164 |
| 5,380,290 A | * | 1/1995 | Makower et al. ....... 604/164.01 |
| 5,458,568 A | * | 10/1995 | Racchini et al. ............ 604/19 |
| 5,505,700 A | * | 4/1996 | Leone et al. ........... 604/101.03 |
| 5,569,198 A | | 10/1996 | Racchini ..................... 604/96 |
| 5,571,119 A | * | 11/1996 | Atala ......................... 606/146 |
| 5,628,730 A | | 5/1997 | Shapland et al. ........... 604/21 |
| 5,690,619 A | * | 11/1997 | Erskine ..................... 604/263 |
| 5,693,029 A | | 12/1997 | Leonhardt .................. 604/264 |
| 5,713,863 A | | 2/1998 | Vigil et al. ................. 604/104 |
| 5,746,716 A | | 5/1998 | Vigil et al. .................. 604/97 |
| 5,797,878 A | | 8/1998 | Bleam ....................... 604/196 |
| 5,860,992 A | * | 1/1999 | Daniel et al. .............. 606/145 |
| 5,873,852 A | | 2/1999 | Vigil et al. .................. 604/52 |
| 5,997,504 A | * | 12/1999 | Bell ........................ 604/93.01 |
| 6,001,088 A | * | 12/1999 | Roberts et al. ............. 605/501 |
| 6,050,976 A | * | 4/2000 | Thorne et al. .......... 604/164.01 |
| 6,346,099 B1 | * | 2/2002 | Altman ....................... 604/528 |
| 2002/0002349 A1 | * | 1/2002 | Flaherty et al. ......... 604/164.11 |

FOREIGN PATENT DOCUMENTS

WO      WO01/49357    *   7/2001  .......... A61M/25/10

OTHER PUBLICATIONS

Kwon, et al.; Adventitial Vasa Vasorum in Ballon–injured Coronary Arteries Visualization and Quantitation by a Microscopic Three–dimensional Computed Tomography Technique; American College of Cardiology; JACC, vol. 32., No. 7; pp. 2072–2079; Dec. 1998.

Scott, et al; The Role of Adventitial Vasculature In Restenosis: A New View of an Old Problem; American College of Cardiology; JACC, vol. 32, No. 7; p. 2080; Dec. 1998.

* cited by examiner

Primary Examiner—Teresa Walberg
Assistant Examiner—Leonid Fastovsky
(74) Attorney, Agent, or Firm—Blakely, Sokoloff, Taylor & Zafman LLP

(57) ABSTRACT

A substance delivery apparatus for a catheter assembly is provided. The delivery apparatus includes a base and a needle connected to the base. The needle is capable of pivotally moving with respect to the base for penetrating into tissues of a passageway for administering a therapeutic or bioactive substance to the subject. The needle can pivot in response to inflation of a balloon incorporated with the catheter assembly.

24 Claims, 6 Drawing Sheets

SYRINGE ASSEMBLY FOR A CATHETER

BACKGROUND OF THE INVENTION

1. Field of the Invention

The present invention pertains generally to a medical device useful for delivering a substance to a biological passageway. More specifically, the present invention pertains to a catheter device having a syringe assembly useful for delivering a therapeutic or bioactive substance to a passageway, such as a blood vessel.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the blood vessel wall. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells (SMCs). Excessive neoinitimal tissue formation, characterized by SMC migration and proliferation to the intima, follows the injury. Proliferation and migration of SMCs from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

To reduce the chance of the development of restenosis, therapeutic substances are administered to the treatment site. For example, anticoagulant and antiplatelet agents are commonly used to inhibit the development of restenosis. In order to provide an efficacious concentration to the target site, systemic administration of such medication often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

One commonly applied technique for the local delivery of a therapeutic substance is through the use of a medicated, implantable prosthesis, one example of which includes a stent. A stent coated with a polymeric carrier, which is impregnated with a therapeutic substance, can be implanted at a selected site of treatment. The polymeric carrier allows for a sustained delivery of the therapeutic substance. A disadvantage associated with the use of a medicated stent is that the quantity of the substance that can be impregnated in the polymeric carrier is limited. Increasing the quantity of the substance in the polymeric coating can lead to processing difficulties such as poor adhesion of the coating to the stent surface. In order to increase the capacity of the polymeric carrier, the amount of polymeric material employed, and in effect the thickness of the coating, must be increased to accommodate the quantity of the substance used. An increase in the quantity of the polymeric material and the profile of the coating can perturb the geometrical and mechanical functionality of the stent, as well as limit the applications for which the stent can be used.

Another disadvantage associated with the use of medicated stents is that the polymeric carrier is only capable of applying the therapeutic substance to the inner surface of the tunica intima layer of the vessel. The polymeric carrier is incapable of significantly introducing a therapeutic substance to the tunica adventitia or the tunica media layers of the vessel. There is a need to provide a substance delivery apparatus which is capable of applying any desired amount of therapeutic substances to the tunica adventitia and media layers to inhibit migration of SMCs and the development of ECM.

Another commonly applied technique for the local delivery of a therapeutic substance is through the use of a porous balloon attached to a distal end of a catheter assembly. The expansion of the balloon, which in effect results in the dilation of the occluded region, is accomplished by injecting a therapeutic substance into the balloon. The use of a therapeutic substance as an expansion fluid additionally functions as a medicament for the diseased region, as the therapeutic substance is discharged from the porous balloon during and subsequent to the expansion therapy. A shortcoming associated with this procedure is that the therapeutic substance is contiguously carried off in the patient's blood steam as it is being discharged from the balloon, which results in an ineffective treatment of the target site and adverse exposure of the substance to healthy tissues. There is a need for a substance delivery apparatus that is capable of applying a therapeutic substance to the diseased region without significant loss of the substance caused by the downstream flow of blood.

SUMMARY OF THE INVENTION

In accordance with one aspect of the present invention, a substance delivery apparatus for a catheter assembly is provided which includes a base supported by the catheter assembly and a needle pivotally connected to the base. The needle is used for penetrating into tissues of a passageway for administering a bioactive or therapeutic substance or combination of substances. A coupling element, for example a pin element, pivotally connects the base to the needle. The substance delivery apparatus can additionally include a delivery lumen in fluid communication with the needle. A bioactive or therapeutic substance or a combination of substances can be introduced into the delivery lumen for injection out from the needle. In accordance with one embodiment, the base is made from a hollow tube having a pair of opposing slots cut out at one end of the tube to define an opposing pair of flanges. A portion of one end of the needle, accordingly, can be disposed between and connected to the flanges.

In accordance with one embodiment, the catheter assembly includes a membrane having a pair of opposing ends coupled to a distal end of the catheter assembly to form a chamber. The chamber is in fluid communication with the catheter assembly to allow the membrane to be inflated to an expanded configuration. The membrane can include a first section and a second section. The second section of the membrane can have a thickness less than the thickness of the first section such that when the membrane is inflated, the second section expands outwardly to a greater extent than the first section. The first section can support the base and the second section can cause the needle to pivotally rotate about the coupling element for penetration into tissues of a passageway.

In accordance with one embodiment, the first section of the membrane can include pores. The membrane can additionally include a third section having pores, in addition to or in lieu of a porous first section. The pores can allow for the discharge of a bioactive or therapeutic substance that is introduced into the chamber of the expandable membrane.

In accordance with yet another embodiment, the substance delivery apparatus can additionally include a transport element operably supported by the catheter assembly. The transport element can have a first electrode element, a second electrode element, and a power supply electrically communicating with the first and second electrode elements. Alternatively, the transport element can be an ultrasonic transducer.

In accordance with another aspect of the present invention, a device for delivering a substance to a desired area of a passageway is provided. The device includes a catheter assembly having a distal end and a proximal end. A membrane having a pair of opposing ends is coupled to the distal end of the catheter assembly to form a chamber. The membrane can be inflated from a collapsed configuration to an expanded configuration. A first syringe assembly is supported by the catheter assembly for allowing a first therapeutic substance to be injected into a tissue of a passageway. The first syringe assembly includes a base, a needle pivitolly coupled to the base, and a hinge member pivitolly coupling the base to the needle. The needle is capable of pivoting from a first position towards a second position in response to the membrane being inflated from the collapsed configuration to the expanded configuration. The needle of the first syringe assembly can also be capable of pivoting from the second position back towards the first position in response to the membrane being deflated. The needle of the first syringe assembly can be configured to penetrate into the tunica media layer of a blood vessel wall for administering the first therapeutic substance to a region of the tunica media layer of the blood vessel wall.

In accordance with one embodiment, the membrane can include a plurality of pores for allowing a second therapeutic substance supplied into the chamber to be discharge out from the pores. The second therapeutic substance can be the same as or different than the first therapeutic substance.

The device can additionally include a second syringe assembly supported by the catheter assembly for allowing a third therapeutic substance to be injected into a tissue of the passageway—the third therapeutic substance being the same as or different than the first therapeutic substance. The second syringe assembly includes a base, a needle pivotally coupled to the base of the second syringe assembly, and a hinge member pivitolly coupling the base to the needle of the second syringe assembly. The needle for the second syringe assembly is capable of pivoting from a first position towards a second position in response to the membrane being inflated from the collapsed configuration to the expanded configuration. The needle of the first syringe assembly can also be capable of pivoting from the second position back towards the first position in response to the membrane being deflated.

DETAILED DESCRIPTION OF THE EMBODIMENTS

APPARATUS

Figure 1:
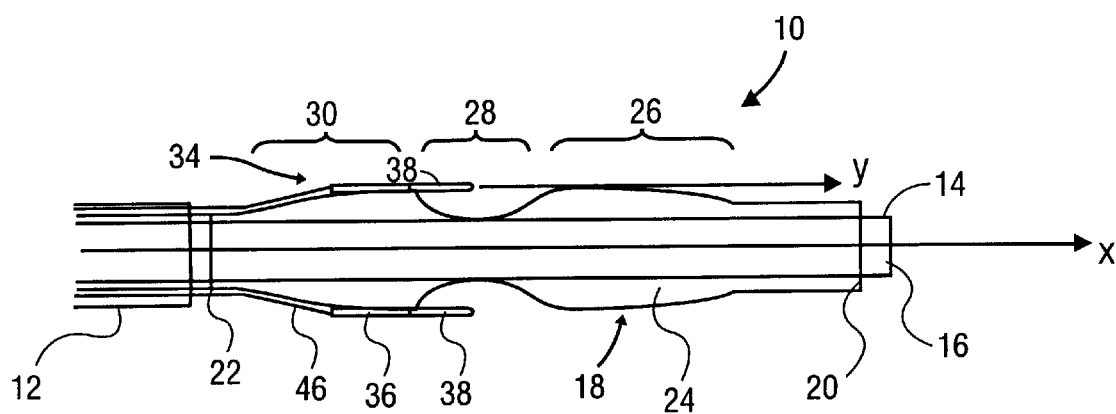
FIG. 1 is a partial sectional view of one embodiment of a substance delivery apparatus of the present invention in the form of a catheter assembly having a balloon in a collapsed configuration and a syringe assembly in a rested position.
Figure 2:
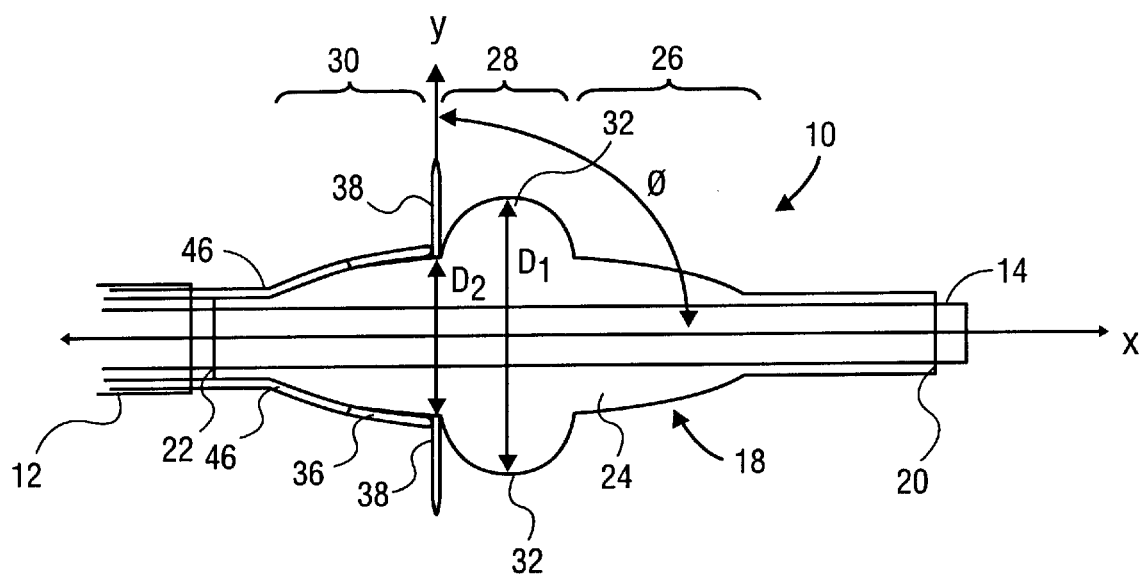
FIG. 2 is a partial sectional view of the delivery apparatus of FIG. 1, illustrating the balloon in an expanded configuration and the syringe assembly pivotally rotated to a delivery position.

Referring now to the drawings, wherein similar parts are identified by like reference numerals, FIGS. 1 and 2 illustrate a substance delivery apparatus 10 in accordance with one embodiment of the invention. In general, substance delivery apparatus 10 provides a system for delivering a substance, such as a bioactive or therapeutic substance or a combination of substances, to or through a desired area of a passageway in order to treat a localized area of the passageway or to treat a localized area of tissue located adjacent to the passageway. Substance delivery apparatus 10 includes a catheter assembly 12, which is intended to broadly include any medical device design for insertion into a body passageway to permit injection and/or withdrawal of fluids, to maintain the patency of the passageway, or for any other purpose. It is contemplated that substance delivery apparatus 10 has applicability for use with any biological passageway, including blood vessels, urinary tract, intestinal tract, kidney ducts, wind pipes, and the like.

Catheter assembly 12 includes an elongated catheter tube 14 having a proximal end (not illustrated) and distal end 16. Catheter assembly 12 can include a guidewire lumen (not illustrated) for allowing catheter assembly 12 to be feed over and maneuvered over a guidewire (not illustrated). One of ordinary skill in the art knows how to implement and use a guidewire with a catheter. A balloon 18 is incorporated at distal end 16 of catheter assembly 12 and is in fluid communication with catheter assembly 12.

Balloon 18 has a pair of opposing ends 20 and 22 engaged to catheter tube 14 to define a balloon chamber 24. Balloon 18 is selectively inflatable to dilate from a collapsed configuration to a desired and controlled expanded configuration. Balloon 18 can be selectively inflated by supplying a fluid into balloon chamber 24 at a predetermined rate of pressure, for example 1–20 atm. Balloon 18 is selectively deflatable, after inflation, to return to the collapsed configuration or a deflated profile. Balloon 18 can be defined by three sections, a distal portion 26, a medial portion 28, and a proximal portion 30. In one embodiment, medial portion 28 has a balloon wall thickness less than the wall thickness of distal 26 and proximal 30 portions. Accordingly, when balloon 18 is inflated, medial portion 28 expands outwardly to a greater extent than distal 26 and proximal 30 portions to form a bulbous protrusion 32, as illustrated in FIG. 2. It should be noted that the Figures are not to scale and that the elements have been over or under emphasized for illustrative purposes.

Distal 26, medial 28 and proximal 30 portions can have a balloon wall of any suitable thickness so long as the thickness does not compromise properties that are critical for achieving optimum performance. The properties include high burst strength, low compliance, good flexibility, high resistance to fatigue, the ability to fold, the ability to cross and recross a desired region of treatment or an occluded region in a lumen, and low susceptibility to defect caused by handling. In a deflated configuration, medial portion 28 can have a balloon wall thickness of, for example, about 30% to about 70% less than the thickness of the balloon wall for distal 26 and proximal 30 portions. Exemplary specifications of the balloon wall thickness for medial portion 28 can be form about 0.007 mm to about 0.018 mm.

In the optimum expanded configuration under which balloon 18 was designed to be used, the diameter $D_1$ of the largest section of bulbous protrusion 32 can be, by way of example, about 20% greater than the diameter $D_2$ of the largest section of distal 26 or proximal 30 portions. The largest diameter $D_1$ of medial portion 28, in an expanded configuration, can be, for example, in the range of about 3.5 mm to about 10 mm. The length of balloon 18 can be, for example, in the range of about 3 mm to about 40 mm, with medial portion 28 consisting of, for example, about 7.5% to about 99% of the total length of balloon 18. The specific specifications of balloon 18 depend on the procedure for which balloon 18 is to be used and the anatomy and size of the target lumen in which balloon 18 is to be inserted.

Distal 26, medial 28, and proximal 30 portions can be bound together by seams or be made out of a single seamless material. As a single seamless material, balloon 18 can be made from extrusion methods known to one or ordinary skill in the art. Balloon 18 can be made from any suitable material, including, but not limited to, polymers and copolymers of polyolefins, polyamides, polyesters and the like. The specific material employed must be mutually compatible with the fluids employed in conjunction with balloon 18 and must be able to stand the pressures that are developed within balloon chamber 24.

In accordance with another embodiment of the invention, any section of the wall of balloon 18 can include pores. The pores can have a wide range in size, for example from about 10 Å to less than about 5 $\mu$ in diameter. The pore density can be in any suitable range, typically in the range of about $10^2$ to about $10_6$ pores per $cm^3$. To inflate balloon 18, a fluid, containing a therapeutic or bioactive substance, is supplied into chamber 24 at a predetermined pressure, for example about 4 atm. During inflation, the pressure should not exceed, for example, about 20 atm so as to prevent significant leakage of the fluid from the pores. The specific pressure depends of factors such as the size of the pores, the thickness of the balloon wall, the material from which the balloon wall is made, the type and viscosity of substance employed, and the flow rate that is desired. Significant amount of leakage of the fluid during inflation is a drawback because the therapeutic or bioactive substance will get carried off in the patient's blood stream which results in an ineffective treatment of the diseased region and exposure of the substance to healthy tissues. Porous balloon can be used to deliver a substance to the tissues at a desired flow rate.

In accordance with another embodiment, only designated areas of the wall of balloon 18 at proximal 26 and/or distal portion 30 are made from a porous membrane—medial 28 portion of the balloon wall being made from a non-porous membrane. The inflation of balloon 18 causes bulbous protrusion 32 to engage against the vessel wall for blocking the flow of blood. Therapeutic or bioactive substances secreted from proximal 26 and/or distal 30 portions are prevented from being contiguously carried off by the blood stream, thus increasing the residence time of exposure to the diseased legion.

The flow rate of a substance is determined in units of ml/min and is dependent upon flow parameters such as pore density, pore size, viscosity of the composition, and applied pressure. As a general rule, flow parameters can be interrelated in the following manner: The flow rate is proportional to the pore density if all other flow parameters are constant; the flow rate is proportional to the diameter of the pore raised by the power of four; the flow rate is inversely proportional to the viscosity of the composition used; and the flow rate is proportional to the applied pressure.

Pore size of about 10 Å to about 5 $\mu$ reduces the velocity at which the fluid is capable of traveling through a given pore, as compared to balloons having larger pore sizes, to prevent "jetting effect" that have significantly hindered the effectiveness of balloons having the larger pore sizes. "Jetting effect" is the velocity of liquid through a pore of a selected size at which trauma to the tissues occurs. The flow rate of delivery can be increased without increasing the velocity of the fluid through the pores. The flow rate of a fluid can be increased by increasing the pore density, which will provide the desired effect and delivery rate without increasing the fluid velocity.

Delivery apparatus 10 includes a syringe assembly 34 for injecting a therapeutic or bioactive substance or a combination of substances into tissues of a biological passageway. Referring to FIGS. 3–7, syringe assembly 34 can include a hollow, cylindrical base 36 which can be mounted on distal 26 or proximal 30 portion of balloon 18. Base 36 includes a pair of opposing slots 38A and 38B cut out at one end of base 36 to create a pair of opposing flanges 40. Flanges 40 can be best described as a pair of opposing rectangular arms protruding from one end of base 36. Base 36 can be made out of any suitable metallic or polymeric material. One suitable example includes stainless steel. The dimensional specification of base 36 is not of critical importance. The inner distance between opposing flanges 40 should be capable of receiving at least a portion of a needle 38.

Figure 4:
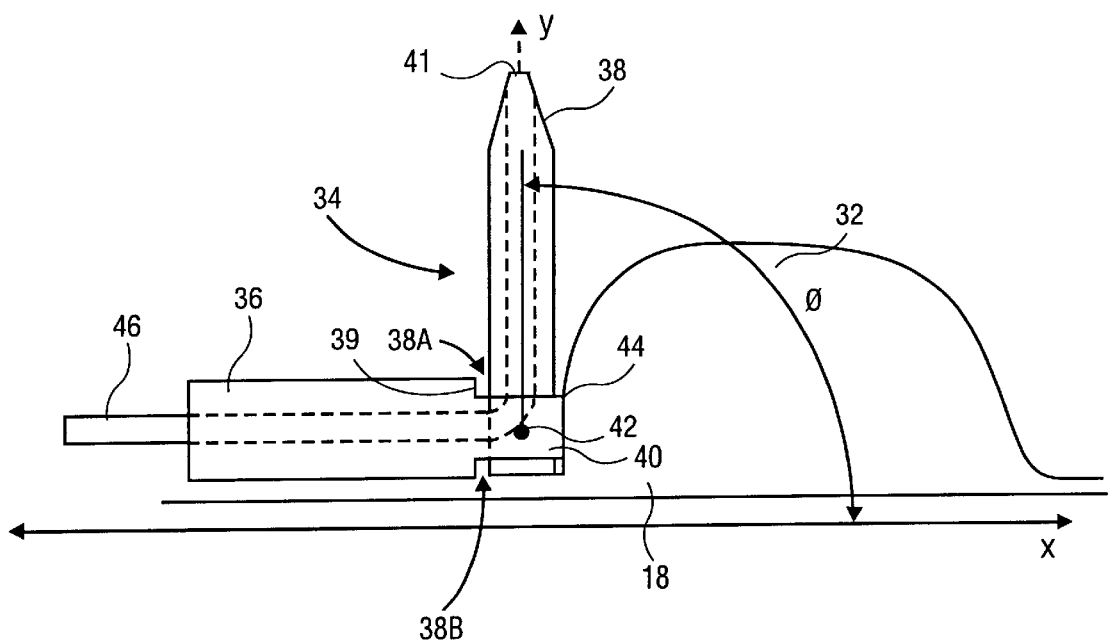
FIG. 4 is a side view of the syringe assembly of FIG. 3 pivotally rotated to a delivery position by the expansion of the balloon.
Figure 5:
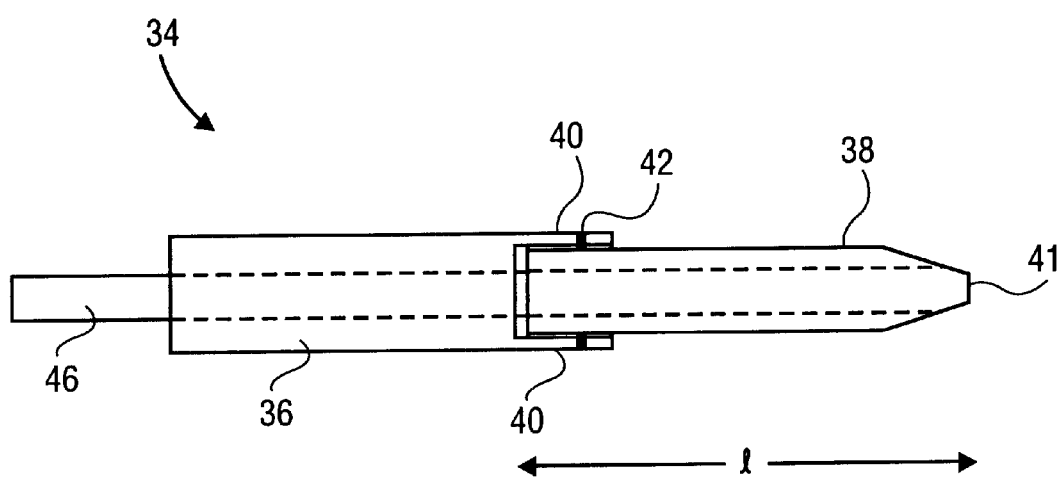
FIG. 5 is a top plan view of one embodiment of the syringe assembly.
Figure 6:
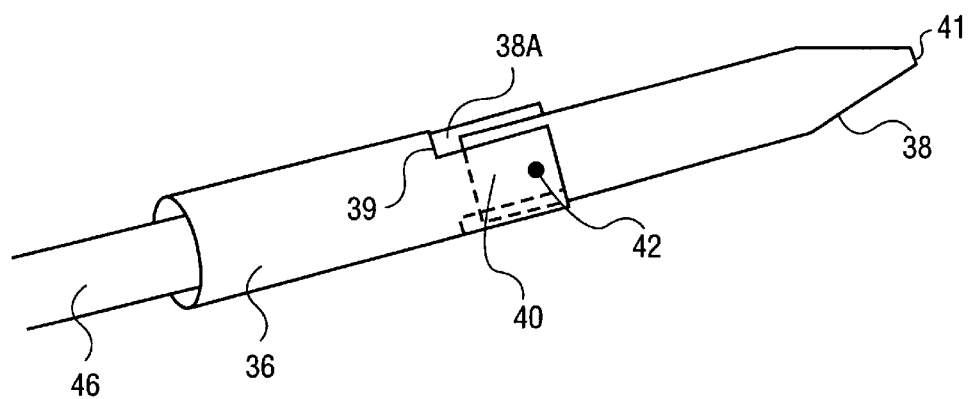
FIG. 6 is a perspective view of one embodiment of the syringe assembly.
Figure 7:
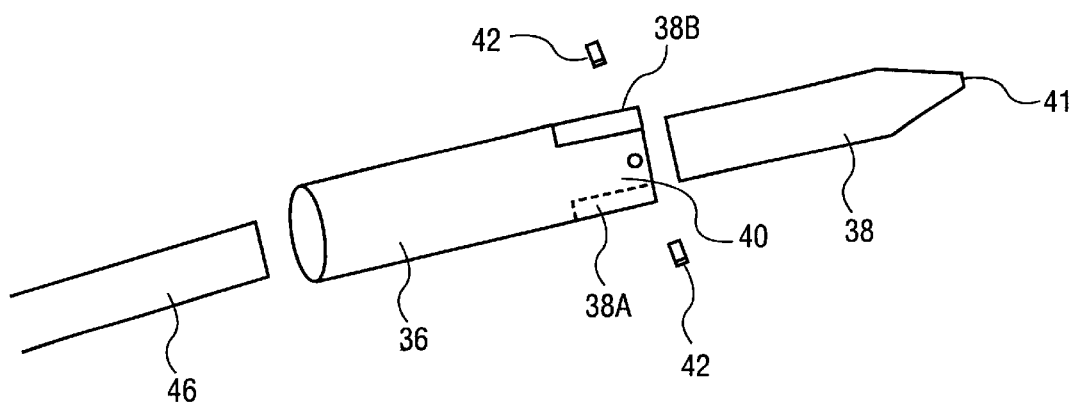
FIG. 7 is an exploded view of one embodiment of the syringe assembly.

Needle 38 is pivitolly coupled to base 36. A hinge member, such as pin elements 42, provides one means for coupling needle 38 to opposing flanges 40. Other coupling means, such as bearings can be used to connect the components. Needle 38 is configured to rotate or pivot about pin member 40 in response to the expansion and retraction of balloon 18, more particularly in response to bulbous protrusion 32. As best illustrated in FIG. 4, an adhesive contact 44 can be used to attach a part of needle 38 to bulbous protrusion 32 to facilitate the retraction of needle 38 when balloon 18 is deflated.

Figure 3:
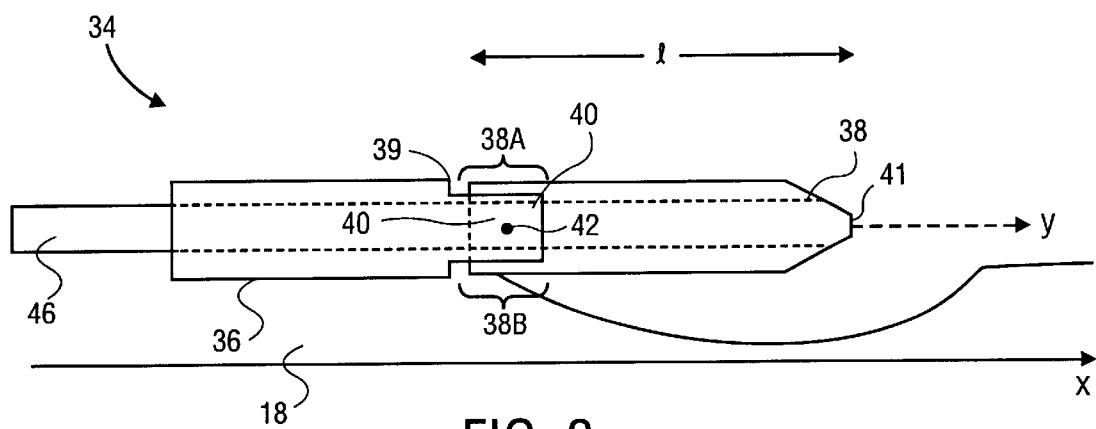
FIG. 3 is a side view of one embodiment of the syringe assembly in a rested position.

In the collapsed configuration of balloon 18, as illustrated in FIGS. 1 and 3, needle 38 of syringe assembly 34 can be in a rested position, or in other words a longitudinal axis y of needle 38 can be generally parallel to longitudinal axis x of balloon 18. As illustrated in FIGS. 2 and 4, the dilation of balloon 18 causes bulbous protrusion 32 to pivot needle 38 of syringe assembly 34 towards a selected delivery position, causing needle 38 to penetrate into a lumen wall. In accordance with one embodiment, the dilation of balloon 18 causes bulbous protrusion 32 to pivot needle 38 towards a selected delivery position, wherein thereafter, further inflation of balloon 18 causes needle 38 to penetrate into a lumen wall. In other words, expansion of bulbous protrusion 32 positions needle 38 at a selected delivery angle and further expansion of distal 26 and/or proximal 30 portions, on which base 36 may be located, will push needle 38 into the tissues.

The extent of the rotation of needle 38 is dependent upon the extent to which bulbous protrusion 32 is inflated. At the delivery position, angle Φ can be about 90°. In an alternative embodiments, the delivery position can be at any suitable angle Φ, typically between greater than about 45° to less than 90°. Referring to FIGS. 3 and 4, edge 39 of slot 38A can serve as a stop for preventing needle 38 from rotating greater than about 90°.

Figure 8A:
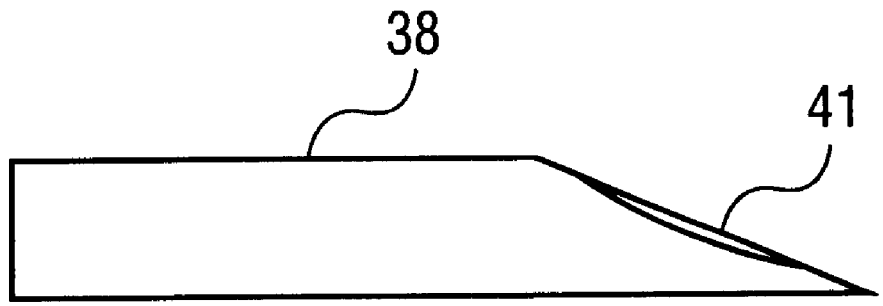
FIG. 8A is one embodiment of a needle for the syringe assembly.
Figure 8B:
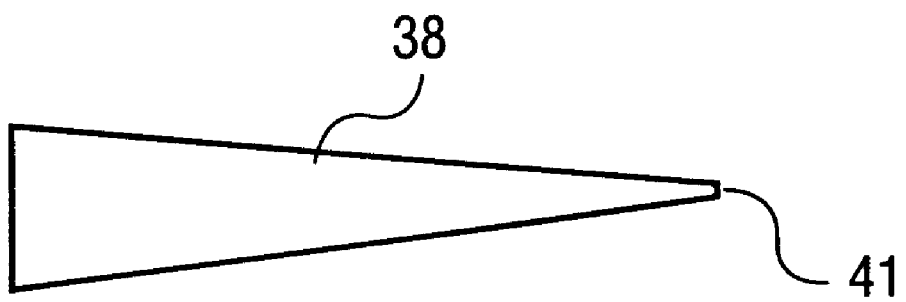
FIG. 8B is another embodiment of a needle for the syringe assembly.

Needle 38 can be of any predetermined length l, the specific length l dependent upon the desired depth of calibrated penetration and the procedure for which syringe assembly 34 is to be used. Additionally, needle 38 should be long enough so as to clear the maximum peak of bulbous protrusion 32 in its expanded state. For example needle 38 should extend about 0.5 mm to about 1.5 mm beyond the outermost point of bulbous protrusion 32 in the selected expanded state of bulbous protrusion 32. Needle 38 can have any suitable geometrical configuration, useful examples of which include a cylindrical body having a conical tip, as illustrated in FIGS. 3–7; a cylindrical body having a tapered tip, as illustrated in FIG. 8A; or a conically shaped body, tapering towards the penetrating tip, as illustrated in FIG. 8B. Needle 38 can be made from any suitable material, including stainless steel. Needle 38 includes an opening 41, of any suitable diameter, for allowing substances to inject out from needle 38.

In one embodiment, delivery apparatus 10 can include any suitable number of pivotally activated syringe assemblies 34 disposed about the periphery of balloon 18. Each of syringe assemblies 34 can be in fluid communication with a designated delivery lumen 46. Delivery lumens 46 can be in fluid communication with one another and/or in fluid communication with a common source of supply of a therapeutic or bioactive substance. Each of syringe assemblies 34 is, therefore, capable of injecting the same substance or the same combination of substances.

In an alternative embodiment, delivery lumens 46 are not in fluid communication with one another. Each of delivery lumens 46 is in fluid communication with a different source of supply of a therapeutic or bioactive substance. Accordingly, each of syringe assemblies 34 will be capable of delivering a different substance or different combinations of substances.

Figure 9:
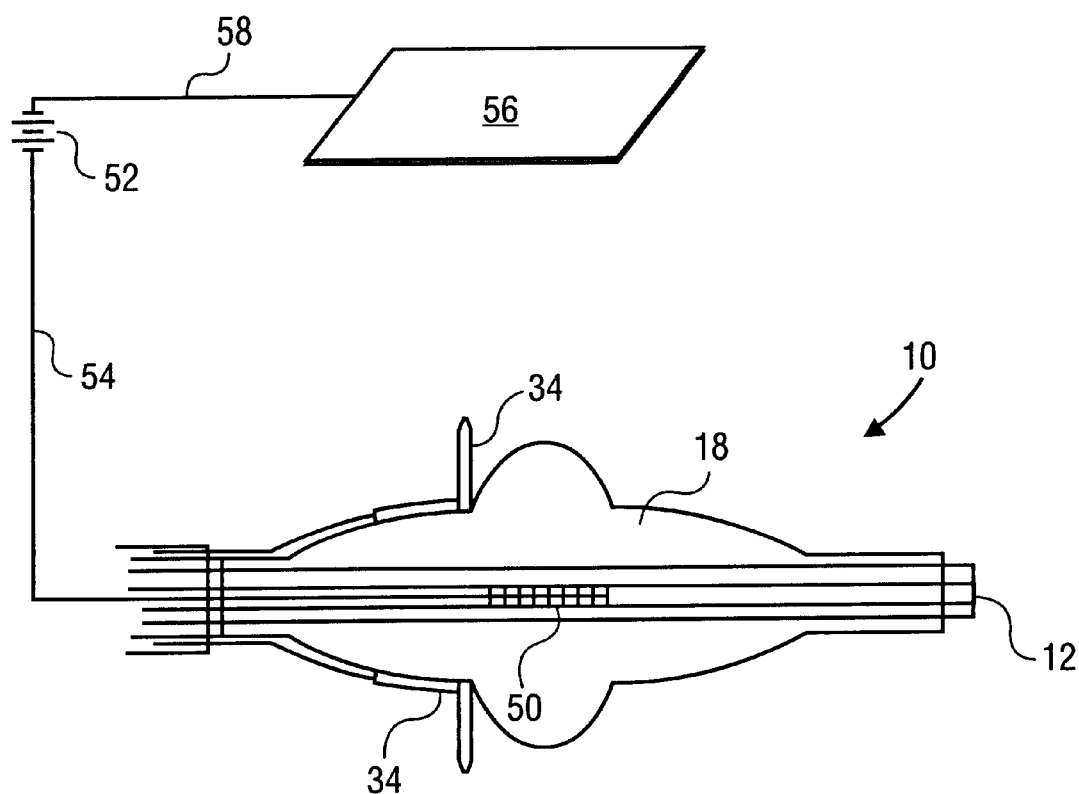
FIG. 9 is a partial sectional view of another embodiment of a substance delivery apparatus of the present invention in the form of a catheter assembly having a balloon in an expanded configuration and a syringe assembly pivotally rotated to a delivery position, the delivery apparatus includes an iontophoresis element for providing a transport force for the substance delivered.

In one embodiment, as illustrated by FIG. 9, iontophoresis technology, as is understood by one of ordinary skill in the art, can be used to drive ionic agents or drag nonionic agents that are in an ionic solution. In order for iontophoresis techniques to be utilized, the substance to be delivered should have an ionic nature or be bound to other ionic molecules. Iontophoresis can, for example, facilitate both transport of a substance across the porous membrane of balloon 18 and/or enhance tissue penetration of the substance. Referring to FIG. 9, a first electrode 50 can be located within balloon 18 and is connected to a power supply 52 by a first lead 54. A second electrode 56 can be located either on the surface of or within the subject's body and is connected to power supply 52 by a second lead 58. The power supply provides an electric signal between first and second electrodes 50 and 56. The signal can be direct or have a particular wave form. Examples of possible wave forms include a rectangular wave having a frequency of about 10 Hz or greater. Additionally, a series of waves can be intermittently passed between first and second electrodes 50 and 56 during the process of delivering the substance.

Figure 10:
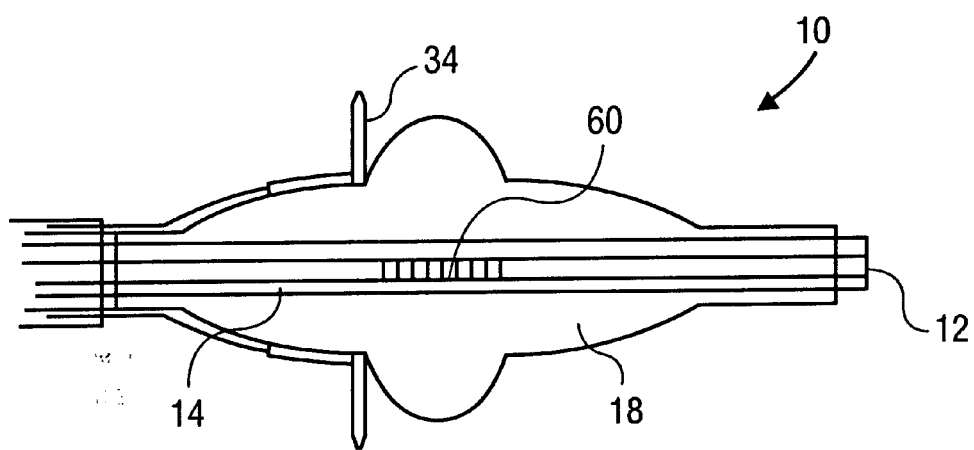
FIG. 10 is a partial sectional view of another embodiment of a substance delivery apparatus of the present invention in the form of catheter assembly having a balloon in an expanded configuration and a syringe assembly pivotally rotated to a delivery position, the delivery apparatus includes an ultrasonic transducer.

In another embodiment, as illustrated in FIG. 10, ultrasonic or high frequency sound waves can be used to transport a substance through the porous membrane and/or into the surrounding tissue. Phonophoresis or sonophoresis has several advantages over iontophoresis, including the ability to achieve greater penetration into internal tissues of the vessel wall. Phonophoresis is also not limited to delivering only ionically charged forms of the substance.

In addition to delivering a substance, ultrasound is advantageous because it can increase tissue temperature and capillary and cellular permeability. These results can enhance intra-tissue transport of a substance, enhance cellular uptake, and cause vasodilation/relaxation, which may be beneficial in vascular applications. As is understood by one of ordinary skill in the art, an ultrasonic piezoelectric transducer 60 such as barium titanate, lead zirconate titanate, or the like, can be disposed within balloon 18. Transducer 60 can be connected to a power supply through catheter tube 14. As a general rule, the diffusion rate of substances delivered by phonophoresis depends on the type of substances and the intensity and frequency of the ultrasonic field. Phonophoretic delivery techniques employ various frequencies of sonic waves, e.g., about 1 MHz or less.

METHOD OF USE

An application of the various embodiments of the present invention will be generally described by way of example with reference to the treatment of a blood vessel having an occluded region. One of ordinary skill in the art should realize that the various embodiments of the present invention could be used in a variety of other medical applications.

Catheter 12 can be advanced along a guidewire so that balloon 18 overlays the stenotic lesion. Balloon 18 can be inflated by introducing an inflation fluid into chamber 24. With a porous balloon membrane, the inflation fluid can be a solution containing a therapeutic or bioactive substance or a combination of substances. When balloon 18 is dilating to the expanded configuration, bulbous protrusion 32 causes needle 38 to rotatably pivot outwardly about pin members 42, away from balloon 18. Needle 38 penetrates into the tissues of the vessel at a calibrated depth. Alternatively, first, needle 38 pivots outwardly about pin member 42 to a selected delivery position, but does not penetrate into the tissues. Second, balloon 18 is further expanded causing needle 38 to penetrate into the tissue of the vessel at a calibrated depth. The depth can be controlled by the degree of inflation of balloon 18.

Balloon 18 can also be used for remodeling of the vessel wall to increase the flow of blood. Prior to the introduction of one of the embodiments of substance delivery apparatus 10 of the present invention, a conventional catheter assembly, having a balloon, can also be used for the expansion therapy.

The walls of a blood vessel are composed of three tunics: tunica intima composed of squamous epithelium called endothelium underlain by a subendothelial layer of loose connective tissues; tunica media, separated from the tunica intima by an internal elastic lamina, is made from smooth muscle cells (SMC) and elastic fibers; and tunica adventitia, the outer most layer, consists chiefly of connective tissues with irregularly arranged elastic and collagenous fibers. Proliferation and migration of SMCs from the tunica media to the tunica intima causes an excessive production of extra cellular matrices (ECM), which is believed to be one of the leading contributors to the development of restenosis. Usefully, needle 38 should be calibrated so that it is capable of penetrating into the tunica media layer to inhibit proliferation and/or migration of SMCs and the development of ECM.

A therapeutic or bioactive substance or a combination of substances can be administered to the adventitia layer and/or the media layer via needle 38 by introducing the substance(s) through delivery lumen 46 at a selected pressure. Virtually any type of useful substance of any given molecular size and weight can be injected through needle 38. Substances having a molecular weight of less that about 5000 daltons are capable of penetrating through the intima layer. Thus, balloon 18 having the porous membrane can be used to administer such substances to the outer layers of the vessel wall.

Therapeutic substances or agents can include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include actinomycin D, angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, dexamethasone, and growth factors such as FGF, PDGF, and VEGF. While the foregoing therapeutic substances or agents are well known for their preventative and treatment properties, the substances or agents are provided by way of example and are not meant to be limiting. Other therapeutic substances which are currently available or that may be developed are equally applicable for use with the present invention. The treatment of patients using the above-mentioned medicines is well known to those of ordinary skill in the art.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A substance delivery apparatus for a catheter assembly, comprising:
    (a) a base supported by said catheter assembly;
    (b) a needle pivotally connected to said base for penetrating into tissues of a passageway for administering a substance to said passageway;
    (c) a coupling element for pivotally connecting said base to said needle; and
    (d) a balloon connected to said base wherein a dilation of said balloon causes said needle to pivot about said coupling element.

2. The substance delivery apparatus of claim 1, wherein said coupling element is a pin element.

3. The substance delivery apparatus of claim 1, wherein said base comprises a hollow tube having a pair of opposing slots cut out at one end of said tube to define an opposing pair of flanges, wherein a portion of one end of said needle is disposed between and connected to said flanges.

4. The substance delivery apparatus of claim 1, wherein said balloon being selectively inflatable to dilate from a collapsed configuration to a desired expanded configuration and said balloon being selectively deflatable, after inflation, to return to said collapsed configuration or a deflated profile and wherein said needle pivotally rotates about said coupling element in response to inflation of said balloon.

5. The substance delivery apparatus of claim 4, wherein at least a selected area of said balloon is made from a porous membrane.

6. The substance delivery apparatus of claim 1, wherein said balloon is a membrane which further comprises:
    a pair of opposing ends coupled to a distal end of said catheter assembly to form a chamber, said chamber being in fluid communication with said catheter assembly to allow said membrane to be inflated to an expanded configuration; and
    a first section and a second section;
    wherein said base is supported by said first section; and
    wherein said second section of said membrane has a thickness less than the thickness of said first section such that when said membrane is inflated, said second section expands outwardly to a greater extent than said first section to cause said needle to pivotally rotate about said coupling element.

7. The substance delivery apparatus of claim 6, wherein said first section of said membrane includes pores.

8. The substance delivery apparatus of claim 6, wherein said membrane additionally comprises a third section, said third section of said membrane having porous.

9. The substance delivery apparatus of claim 1, additionally comprising a transport element operably supported by said catheter assembly, said transport element having a first electrode element, a second electrode element, and a power supply electrically communicating with said first and second electrode elements.

10. The substance delivery apparatus of claim 1, additionally comprising an ultrasonic transducer operably supported by said catheter assembly.

11. The substance delivery apparatus of claim 1, additionally comprising a delivery lumen in fluid communication with said needle, wherein a substance is introduced into said delivery lumen for injection out from said needle.

12. A device for delivering a substance to a desired area of a passageway, comprising:
   (a) a catheter assembly having a distal end and a proximal end;
   (b) a membrane having a pair of opposing ends coupled to said distal end of said catheter assembly to form a chamber, said membrane can be inflated from a collapsed configuration to an expanded configuration; and
   (c) a first syringe assembly supported by said catheter assembly for allowing a first therapeutic substance to be injected into a tissue of a passageway, wherein said first syringe assembly comprises a base, a needle pivitolly coupled to said base, and a hinge member pivitolly coupling said base to said needle,
      wherein said needle is capable of pivoting from a first position towards a second position in response to said membrane being inflated from said collapsed configuration to said expanded configuration.

13. The device of claim 12, wherein said needle of said first syringe assembly is capable of pivoting from said second position back towards said first position in response to said membrane being deflated.

14. The device of claim 12, wherein said needle of said first syringe assembly is configured to penetrate into the tunica media layer of a blood vessel for administering said first therapeutic substance to a region of the tunica media layer of said blood vessel.

15. The device of claim 12, wherein said membrane comprises a plurality of pores for allowing a second therapeutic substance supplied into said chamber to be discharge out from said pores.

16. The device of claim 15, wherein said second therapeutic substance is different than said first therapeutic substance.

17. The device of claim 12, additionally comprising a second syringe assembly supported by said catheter assembly for allowing a second therapeutic substance to be injected into a tissue of said passageway, said second therapeutic substance being different than said first therapeutic substance, wherein said second syringe assembly comprises a base, a needle pivotally coupled to said base of said second syringe assembly, and a hinge member pivitolly coupling said base to said needle of said second syringe assembly,
   wherein said needle for said second syringe assembly is capable of pivoting from a first position towards a second position in response to said membrane being inflated from said collapsed configuration to said expanded configuration.

18. The device of claim 12, wherein said membrane comprising a first section and a second section,
   wherein said base is supported by said first section; and
   wherein said second section of said membrane has a thickness less than the thickness of said first section such that when said membrane is inflated, said second section forms a bulbous bulge for pivotally rotating said needle about said hinge member.

19. The substance delivery apparatus of claim 18, wherein said first section of said membrane has pores to allow a second therapeutic substance supplied into said chamber to be discharged from said membrane.

20. The substance delivery apparatus of claim 18, wherein said membrane additionally comprises a third section, said third section of said membrane having pores to allow a second therapeutic substance supplied into said chamber to be discharged from said membrane.

21. The device of claim 12, additionally comprising a transport element operably connected to said catheter assembly, said transport element having a first electrode element, a second electrode element, and a power supply electrically communicating with said first and second electrode elements, wherein said first electrode element is positioned within said membrane.

22. The device of claim 12, additionally comprising an ultrasonic transducer operably connected to said catheter assembly and positioned within said membrane.

23. A medical assembly, comprising:
   (a) a catheter assembly capable of being guided through anatomical passageways of a subject; and
   (b) a selectively inflatable tubular membrane having ends engaged to a distal end of said catheter assembly to define a chamber bounded by said ends of said membrane, wherein said membrane is defined by a first region and a second region, said second region having a wall thickness smaller than a wall thickness of said first region.

24. The medical assembly of claim 23, additionally comprising a syringe assembly having a base supported by said catheter assembly and a needle pivotally connected to said base,
   wherein said needle pivots away from said catheter assembly in response to inflating said membrane.

* * * * *